(12) United States Patent
Yamada

(10) Patent No.: US 10,535,507 B2
(45) Date of Patent: Jan. 14, 2020

(54) DATA PROCESSING DEVICE AND DATA PROCESSING METHOD

(71) Applicant: SHIMADZU CORPORATION, Kyoto-shi, Kyoto (JP)

(72) Inventor: Yohei Yamada, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 1058 days.

(21) Appl. No.: 14/769,139

(22) PCT Filed: Feb. 22, 2013

(86) PCT No.: PCT/JP2013/054465
§ 371 (c)(1),
(2) Date: Aug. 20, 2015

(87) PCT Pub. No.: WO2014/128912
PCT Pub. Date: Aug. 28, 2014

(65) Prior Publication Data
US 2015/0380225 A1    Dec. 31, 2015

(51) Int. Cl.
*H01J 49/00* (2006.01)
*G16C 20/20* (2019.01)

(52) U.S. Cl.
CPC .......... *H01J 49/0036* (2013.01); *G16C 20/20* (2019.02)

(58) Field of Classification Search
CPC ................ G06F 19/703; H01J 49/0036
See application file for complete search history.

(56) References Cited

U.S. PATENT DOCUMENTS

2005/0159902 A1* 7/2005 Ogata ................. H01J 49/0036
702/30
2005/0261838 A1* 11/2005 Andreev ............ G01N 30/8603
702/22

FOREIGN PATENT DOCUMENTS

EP          1626274 A1    2/2006
JP       2005-201835 A    7/2005
(Continued)

OTHER PUBLICATIONS

Stein S. E. et al: "Optimization and testing of mass spectral library search algorithms for compound identification", Journal of the American Society for Mass Spectrometry, Elsevier Science Inc, US, vol. 5, No. 9, Sep. 1994 (Jan. 9, 1994), pp. 859-866.*
(Continued)

*Primary Examiner* — Alexander Satanovsky
(74) *Attorney, Agent, or Firm* — Sughrue Mion, PLLC

(57) ABSTRACT

A data processing device (1) is provided with: a data base storage region (32c) for storing $MS^n$ mass spectra of a great number of known compounds in advance; an acquisition unit for acquiring the $MS^n$ mass spectrum of an unknown compound (31a); and a score calculation unit (31d) for finding respective scores indicating similarities between the $MS^n$ mass spectrum of the unknown compound and $MS^n$ mass spectra of the great number of known compounds. The data processing device (1) is characterized by being further provided with: an intensity score calculation unit (31b) for classifying the peaks in the $MS^n$ mass spectrum of the unknown compound and the peaks in the $MS^n$ mass spectra of the known compounds into intensity scores of several ranks depending on the dimensions of the ion intensities, respectively; and a position score calculation unit (31c) for finding the respective position scores indicating error in the mass-to-charge ratio for each peak, wherein the score calculation unit (31d) adds up the intensity score of each peak (Continued)

in the MS$^n$ mass spectrum of a known compound, the intensity score of the corresponding peak in the MS$^n$ mass spectrum of the unknown compound and the position score, and calculates as a score the sum total of the values that have been added up for all peaks.

11 Claims, 4 Drawing Sheets

(56) References Cited

FOREIGN PATENT DOCUMENTS

| JP | 2011220773 A | 11/2011 |
|---|---|---|
| JP | O2011220773 | * 11/2011 |

OTHER PUBLICATIONS

Stephen E. Stein et al., "Optimization and Testing of Mass Spectral Library Search Algorithms for Compound Identification", J Am Soc Mass Spectrom, 1994, pp. 859-866, vol. 5.

International Search Report for PCT/JP2013/054465 dated Apr. 9, 2013.

Communication dated Sep. 15, 2016, issued by the European Patent Office in corresponding European Application No. 13875481.7.

\* cited by examiner

DATA PROCESSING DEVICE AND DATA PROCESSING METHOD

CROSS REFERENCE TO RELATED APPLICATIONS

This application is a National Stage of International Application No. PCT/JP2013/054465 filed Feb. 22, 2013, the contents of which are incorporated herein by reference in their entirety.

TECHNICAL FIELD

The present invention relates to a data processing method for finding respective scores indicating similarities between an MS$^n$ mass spectrum of an unknown compound that has been attained by a mass spectrometer and MS$^n$ mass spectra of a great number of known compounds so as to identify the unknown compound on the basis of the scores as well as to a data processing device using the same.

BACKGROUND ART

A technique called MS/MS analysis (MS$^2$ analysis) has been known in the field of mass spectrometry using an ion trap-type mass spectrometer. In general MS$^2$ analysis, first a target ion having a specific mass-to-charge ratio (m/z) is selected from the unknown compound to be analyzed as a precursor ion (parent ion) and the selected precursor ion is fragmented through collision induced disassociation (CID) so as to generated fragmented ions. The manner in which the ion fragments depends on the chemical structure and, therefore, the MS$^2$ mass spectrum of the unknown compound (information on the chemical structure) can be acquired through mass spectrometry of the fragmented ions that have been generated through fragmentation.

In recent years, unknown compounds to be identified, such as of a medicine, of a pesticide or of a protein, have a large molecular weight and also have a complicated chemical structure. Therefore, in some cases, ions do not fragment into fragmented ions having a sufficiently small mass using only a one-step fragmenting operation depending on the type of the unknown compound. In such a case, the fragmenting operation is repeated a number of times and, thus, mass spectrometry is carried out on the generated fragmented ions through MS$^n$ analysis.

A pattern matching process using a data base has been carried out as an analysis process for estimating the chemical structure of the unknown compound from the MS$^n$ mass spectrum gained through the above described MS$^n$ analysis (see Patent Document 1 and Non-Patent Document 1). The data base includes the names and the chemical structures of a great number of compounds (known compounds) and the MS$^n$ mass spectra of these known compounds. In the pattern matching process the MS$^n$ mass spectra of the known compounds and the MS$^n$ mass spectrum of an unknown compound are compared so as to find the respective scores indicating similarities between the MS$^n$ mass spectrum of the unknown compound and the MS$^n$ mass spectra of the great number of known compounds using weighted inner products and the probabilities of occurrences of peaks. As a result, the unknown compounds are aligned in the descending order of scores and, thus, the person conducting the measurement identifies the unknown compound.

PRIOR ART DOCUMENTS

Patent Document

Patent Document 1: Japanese Unexamined Patent Publication 2005-201835

Non-Patent Document

Non-Patent Document 1: Stephen E. Stein, and Donald R. Scott "Optimization and Testing of Mass Spectral Library Search Algorithms for Compound Identification" 1994, American Society for Mass Spectrometry, 859-866.

SUMMARY OF THE INVENTION

Problem to be Solved by the Invention

Even in the case wherein the same compounds are MS$^n$ analyzed, the gained MS$^n$ mass spectra may differ from each other. That is to say, in MS$^n$ mass spectra the peak ion intensity I, the positions of the peaks (m/z) and the existence of peaks easily change. Therefore, in the above described pattern matching process the ion intensity I may change greatly, the positions of the peaks may shift or a peak that is supposed to occur may not occur, which lowers the score. As a result, the similarities between the MS$^n$ mass spectrum of the unknown compound and the MS$^n$ mass spectra of a great number of known compounds may not be evaluated correctly.

Means for Solving Problem

In order to solve the above described problem the present inventor examined a search method for correctly evaluating similarities between the MS$^n$ mass spectrum of an unknown compound and the MS$^n$ mass spectra of a great number of unknown compounds. It was found that in the pattern matching process as described above, the fact is not taken into consideration that the ion intensities I of the peaks, the positions of the peaks (m/z) and the existence of peaks easily change in MS$^n$ mass spectra and, thus, the scores are lower. Thus, a search method was found wherein the fact is taken into consideration that the ion intensities I of the peaks, the positions of the peaks (m/z) and the existence of peaks easily change in MS$^n$ mass spectra when similarities between the MS$^n$ mass spectrum of an unknown compound and the MS$^n$ mass spectra of a great number of known compounds are evaluated.

That is to say, the data processing device according to the present invention is provided with: a data base storage region for storing MS$^n$ mass spectra of a great number of known compounds in advance; an acquisition unit for acquiring the MS$^n$ mass spectrum of an unknown compound; and a score calculation unit for finding respective scores indicating similarities between the MS$^n$ mass spectrum of the unknown compound and MS$^n$ mass spectra of the great number of known compounds, and is further provided with: an intensity score calculation unit for classifying the peaks in the MS$^n$ mass spectrum of the unknown compound and the peaks in the MS$^n$ mass spectra of the known compounds into intensity scores of several ranks depending on the dimensions of the ion intensities, respectively; a neutral loss calculation unit for finding a peak of the neutral loss in the MS$^n$ mass spectrum of the unknown compound; and a position score calculation unit for finding the respective position scores indicating error in the mass-to-charge ratio for each peak on the basis of the difference between the mass-to-charge ratio of each peak that includes the peak of the above described neutral loss in the MS$^n$ mass spectra of the known compounds and the mass-to-charge ratio of the corresponding peak in the MS$^n$ mass spectrum of the unknown compound, wherein the above described score calculation unit adds up the intensity score of each peak in the MS$^n$ mass spectrum of a known compound, the intensity score of the corresponding peak in the MS$^n$ mass spectrum of the unknown compound and the position score, and calculates as a score the sum total of the values that have been added up for all peaks.

Here, the "MS$^n$ mass spectrum of an unknown compound" is gained when the unknown compound may be MS$^n$ analyzed, and the "MS$^n$ mass spectra of the known compounds" may be gained when the known compounds are MS$^n$ analyzed under the same conditions for the unknown compound (ionization method, fragmentation method, and the like), or may be gained when the known compounds are MS$^n$ analyzed under conditions that are different of those for the unknown compound or may be calculated from the chemical structures of the known compounds.

In the data processing device according to the present invention, first <1> the ion intensities I of peaks are processed as follows. Though the ion intensities I of peaks easily change, the peaks of great ion intensities I are considered to be the peaks of fragmented ions that are easily gained from the compound to be analyzed. Therefore, each peak in the MS$^n$ mass spectrum of the unknown compound is categorized into several ranks (upper rank, middle rank, lower rank, for example) depending on the degree of the ion intensity I and, at the same time, each peak in the MS$^n$ mass spectra of the known compound is categorized into several ranks (upper rank, middle rank, lower rank, for example) depending on the degree of the ion intensity I, respectively. As a result, similar peaks can be found even when the ion intensity I differs.

In addition, whether or not a peak exists easily changes and, therefore, peaks that are in a relationship of neutral loss with each other may exist in some cases even when no peaks exist in the same position (mass-to-charge ratio) in the MS$^n$ mass spectrum of the unknown compound and the MS$^n$ mass spectra of the known compounds. Thus, the neutral loss calculation unit finds a peak of neutral loss from the position of the peak and the mass of a precursor ion for the MS$^n$ mass spectrum of the unknown compound. As a result, peaks can be made to correspond to each other even when a peak that is supposed to exist in the MS$^n$ mass spectrum of the unknown compound does not occur. Here, it is assumed that the ion intensity I of the peak of neutral loss to be added in the MS$^n$ mass spectrum has the same ion intensity I as of the original peak.

Next, <2> the position of a peak (m/z) is processed as follows. The positions of peaks in the MS$^n$ mass spectrum of the unknown compound shift to a certain degree. Therefore, the positions of peaks in the MS$^n$ mass spectrum of a known compound are set as references, and the position score "1.0" is made to correspond to the positions of the peaks within the precision range of the mass spectrometer (−1.0 to 1.0 in the mass spectrometer, −0.005 to 0.005 in the TOF, −0.5 to 0.5 in the tandem quadrupole, for example), and the position score that gradually approaches the position score "0.0" out of the precision range is made to correspond so that a similar peak can be found even if the position of the peak differs.

As described above, the intensity score of each peak in the MS$^n$ mass spectrum of a known compound, the intensity score of the corresponding peak in the MS$^n$ mass spectrum of the unknown compound and the position score are added up so that the sum total of the value that has been added up for all of the peaks is calculated as a score.

Effects of the Invention

As described above, in the data processing device according to the present invention similarities between the MS$^n$ mass spectrum of an unknown compound and the MS$^n$ mass spectra of a great number of known compounds can be correctly evaluated even when the ion intensities I of peaks in the MS$^n$ mass spectrum of the unknown compound and the positions of peaks (m/z) and the existence of peaks change.

Other Means for Solving Problem and Effects Thereof

The data processing device according to the present invention may also be provided with a peak score calculation unit for finding a peak score indicating the degree of matching on the basis of the degree of matching found from the number of matching pairs regarding the mass-to-charge ratio of each peak in the MS$^n$ mass spectrum of a known compound and the mass-to-charge ratio of the corresponding peak in the MS$^n$ mass spectrum of the unknown compound, wherein the above described score calculation unit adds the above described peak score to the above described score.

In the data processing device according to the present invention <3> the degree of matching of a peak/neutral loss pair is process as follows. A peak score indicating the degree of matching is found from the number of pairs that have matched regarding the mass-to-charge ratios of the peaks in the MS$^n$ mass spectra of the known compounds and the mass-to-charge ratios of peaks (including a peak of neutral loss) in the MS$^n$ mass spectrum of the unknown compound ((number of matching peaks/number of peaks in MS$^n$ mass spectra of known compounds)×100, for example).

In addition, in the data processing device according to the present invention, the above described intensity score calculation unit may classify each peak in the MS$^n$ mass spectrum of the unknown compound and each peak in the MS$^n$ mass spectra of the known compounds into intensity scores of three or several ranks, respectively, depending on the ion intensity or the log value transformed from the ion intensity.

Furthermore, in the data processing device according to the present invention, the above described intensity score calculation unit classifies each peak in the MS$^n$ mass spectrum of the unknown compound and each peak in the MS$^n$ mass spectra of the known compounds into intensity scores of several ranks, respectively, depending on the degree of the ion intensity and the value of the mass-to-charge ratio of the peak.

In the data processing device according to the present invention the degree of uniqueness of a peak increases in proportion to the mass-to-charge ratio in an MS$^n$ mass spectrum while a peak having a large mass-to-charge ratio has a small ion intensity in some cases and, therefore, similarities between the MS$^n$ mass spectrum of an unknown compound and the MS$^n$ mass spectra of a great number of known compounds can be correctly evaluated by weighting the ion intensities in accordance with the mass-to-charge ratios (the intensity I of a certain peak is weighted as $I=M\times(I)^{1/2}$ when the ion intensity is I and the mass-to-charge ratio is M, for example).

Moreover, in the data processing device according to the present invention the above described intensity score calculation unit may remove a peak of which the degree of ion intensity is of a threshold value or less from the $MS^n$ mass spectrum of the unknown compound.

In the data processing device according to the present invention, a score can be gained by focusing only on appropriate peaks and, thus, a search having a high reliability can be carried out.

In addition, in the data processing device according to the present invention the above described position score calculation unit may set the mass-to-charge ratio of a peak in the $MS^n$ mass spectra of the known compounds as a reference value and may, respectively, find a position score of which the value is lower as the position is further away from the reference value for each peak in the $MS^n$ mass spectrum of the unknown compound.

In the data processing device according to the present invention an appropriate distribution function wherein the mass-to-charge ratio of a peak in the MSn mass spectrum of a known compound is set as a reference and the value lowers as the position is farther away from the reference, an approximation function wherein the mass-to-charge ratio of a peak in the MSn mass spectrum of a known compound is set as a reference and the value attenuates to the position score "0" with an appropriate inclination, a step function wherein the mass-to-charge ratio of a peak in the MSn mass spectrum of a known compound is set as a reference and the value equals the position score within a specified range and equals the position score "0" outside of the specified range, or a combination of these may be used to, respectively, find the position score for each peak. Here, the mass-to-charge ratio of a peak in the MSn mass spectra of a known compound that is set as a reference is not necessarily a constant value but may be a variable value on the basis of the existence probability or the bonding force found through the calculation of the molecular orbital in the structural formula. In the case wherein there are a number of peaks in the MSn mass spectrum of a known compound in the distribution function, the approximation function or the step function, the peak that is the closest to the reference or the peak that of which the value gained by adding up the intensity score and the position score is the highest may be selected.

As described above, In the data processing device according to the present invention a function of the positions of peaks can be used so that a search having a high reliability can be carried out. In the case wherein the function of the positions of peaks provides a linear distribution, a simple and efficient search can be carried out.

Furthermore, in the data processing device according to the present invention the above described position score calculation unit corrects the mass-to-charge ratio of a peak in the $MS^n$ mass spectrum of the unknown compound using the mass of an adduct ion.

In the data processing device according to the present invention it is possible for the position of a peak to shift by 1 or greater due to an adduct ion (adduct such as —H, —OH, —$CO_2$, or the like). Therefore, a corresponding peak can be found for a peak outside of the precision range so that similar peaks can be found even when the position of a peak shifts by 1 or greater.

Moreover, the above described peak score calculation unit finds a peak score that increases as the number of matching pairs increases.

In the data processing device according to the present invention the degree of effect on the score can be changed in accordance with the number of matching pairs can be altered so that variations of the same compound wherein many partial structures match, such as a metabolite, can be correctly searched.

In addition, in the data processing device according to the present invention the above described score calculation unit may, respectively, find a score of the $MS^{n+m}$ mass spectrum indicating similarity between the $MS^{n+m}$ mass spectrum of the unknown compound and the $MS^{n+m}$ mass spectra of the great number of known compounds, and may add the score of the $MS^{n+m}$ mass spectra to the $MS^n$ mass spectra.

In the data processing device according to the present invention the mass spectra of child and parent ions that have been associated with each other can be reflected in the score and, thus, a search having a high reliability can be carried out.

Furthermore, the data processing method according to the present invention uses a data processing device that includes: a data base storage region for storing $MS^n$ mass spectra of a great number of known compounds in advance; an acquisition unit for acquiring the $MS^n$ mass spectrum of an unknown compound; and a score calculation unit for finding respective scores indicating similarities between the $MS^n$ mass spectrum of the unknown compound and $MS^n$ mass spectra of the great number of known compounds, and includes: an intensity score calculation step of classifying the peaks in the $MS^n$ mass spectrum of the unknown compound and the peaks in the $MS^n$ mass spectra of the known compounds into intensity scores of several ranks depending on the dimensions of the ion intensities, respectively; a neutral loss calculation step of finding a peak of the neutral loss in the $MS^n$ mass spectrum of the unknown compound; a position score calculation step of finding the respective position scores indicating error in the mass-to-charge ratio for each peak on the basis of the difference between the mass-to-charge ratio of each peak that includes the peak of the above described neutral loss in the $MS^n$ mass spectra of the known compounds and the mass-to-charge ratio of the corresponding peak in the $MS^n$ mass spectrum of the unknown compound; and a score calculation step of adding up the intensity score of each peak in the $MS^n$ mass spectrum of a known compound, the intensity score of the corresponding peak in the $MS^n$ mass spectrum of the unknown compound and the position score, and of calculating as a score the sum total of the values that have been added up for all peaks.

Moreover, in the data processing method according to the present invention the data processing method according to the present invention may further include: a peak score calculation step of finding a peak score indicating the degree of matching on the basis of the degree of matching found from the number of matching pairs regarding the mass-to-charge ratio of each peak in the $MS^n$ mass spectrum of a known compound and the mass-to-charge ratio of the corresponding peak in the $MS^n$ mass spectrum of the unknown compound; and an addition step of adding the above described peak score to the above described score.

PREFERRED EMBODIMENTS

In the following embodiments according to the present invention are described in reference to the drawings. Here, the present invention is not limited to the below described embodiments but includes various modifications as long as the gist of the present invention is not deviated from.

Figure 1:
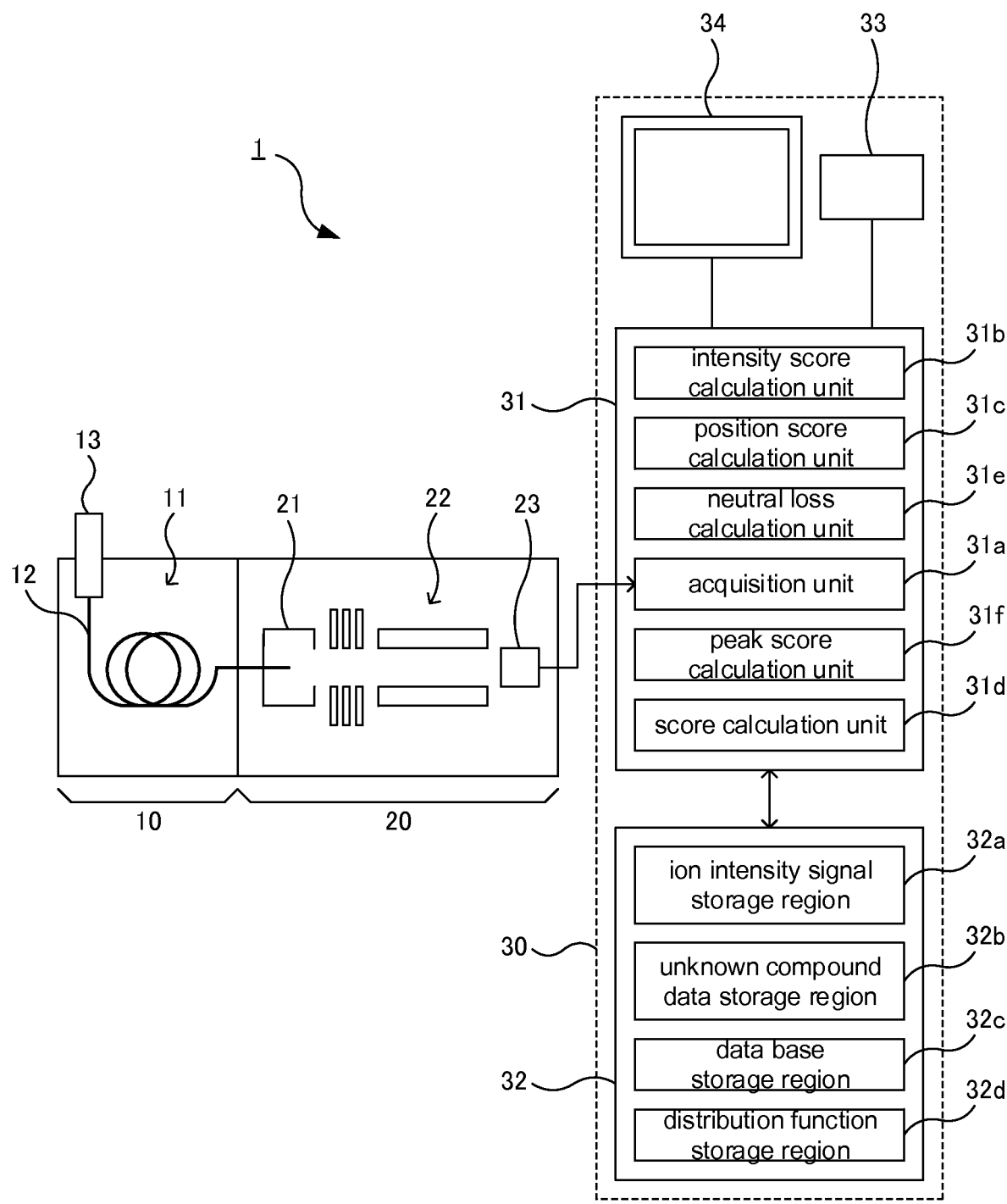
FIG. 1 is a block diagram schematically showing the structure of the mass spectrometer according to one embodiment of the present invention.

FIG. 1 is a block diagram schematically showing the structure of the mass spectrometer according to one embodiment of the present invention.

A liquid chromatography-mass spectrometer (LC/MS) 1 is provided with a liquid chromatographic device (LC) 10, a mass spectrometer (MS) 20 that allows for $MS^n$ analysis and a computer (data processing device) 30.

Though a case wherein a mass spectrum gained by LC/MS 1 is used is cited as an example here, similar descriptions are applied for other cases that utilize other types of chromatography-mass spectrometers, such as a gas chromatography-mass spectrometer (GC/MS), and mass spectrometers into which a sample is directly introduced.

LC 10 is provided with a column oven 11, a column 12 that is equipped inside of the column oven 11 and a sample injection unit 13 that is connected to the entry end of the column 12.

In this LC 10, a sample is pushed by a carrier gas so as to be introduced into the column 12 through the sample injection unit 13. As a result, each component (unknown compound) included in the sample is separated in the direction of the time axis while passing through the column 12 before reaching the exit end of the column 12. Here, the exit end of the column 12 is connected to the MS 20.

The MS 20 is provided with an ion source 21 for ionizing an unknown compound, a mass separation unit that mass separates the generated ions and allows for $MS^n$ analysis and a detector 23 for detecting the mass separated ions. A sonic spray ion source, an ion spray and a matrix-assisted laser desorption/ionization source in addition to an electrospray ion source can be used as the ion source 21. A triple quadrupole mass spectrometer, an ion trap-type mass spectrometer or the like can be used as the mass separation unit 22. Here, an ion having an appropriate mass-to-charge ratio (m/z) is automatically selected as a precursor ion from among the ion originating from each sample component, or an ion having a peak of the mass-to-charge ratio (m/z) that has been designated in advance is selected as a precursor ion in order to carry out mass separation/detection of the fragmented ions that have been generated by fragmenting the precursor ion.

In this MS 20, ions resulting from the ionization in the ion source 21 are introduced into the mass separation unit 22. The mass separation unit 22 mass separates ions. It also sequentially carries out $MS^n$ analysis in accordance with the setting by the person conducting the measurement (n=2, 3, 4, . . . ). The mass separated ions are sent to the detector 23 so as to be detected as an $MS^n$ mass spectrum and the data of the $MS^n$ mass spectrum is sent to the computer 30 (n=2, 3, 4, . . . ).

The computer 30 is provided with a CPU 31, a memory 32, an input device 33 and a display unit 34. The functions processed by the CPU 31 are illustrated as blocks in such a manner that the CPU 31 has an acquisition unit 31a for acquiring data of the $MS^n$ mass spectrum of an unknown compound, an intensity score calculation unit 31b for calculating intensity scores $I_d$ and $I_q$, a position score calculation unit 31c for calculating a position score S(err), a neutral loss calculation unit 31e, a peak score calculation unit 31f for calculating a peak score S(N) and a score calculation unit 31d for calculating a score Scr.

The memory 32 has an ion intensity storage region 32a for storing the ion intensity I, an unknown compound data storage region 32b for storing the $MS^n$ mass spectrum of an unknown compound, a data base storage region 32c for storing the $MS^n$ mass spectra of a great number of known compounds in advance and a distribution function storage region 32d for storing a distribution function for calculating the position score S(err) in advance.

Here, the $MS^n$ mass spectra of known compounds stored in the data base storage region 32c are gained by actually carrying out $MS^n$ analysis on known compounds in MS 20. The $MS^n$ mass spectra are stored in the data base storage region 32c by carrying out $MS^n$ analysis on a great number of known compounds.

In addition, each peak in the $MS^n$ mass spectra of known compounds stored in the data base storage region 32c is categorized into three ranks for the ion intensity $I_d$ depending on the degree of the ion intensity $I_d$ by means of the intensity score calculation unit 31b. Concretely, peaks of which the ion intensity $I_d$ is $I_1$ or greater are categorized as having an intensity score of "4," which is the high rank, peaks of which the ion intensity $I_d$ is $I_2$ or greater and less than $I_1$ are categorized as having an intensity score of "3," which is the middle rank, and peaks of which the ion intensity $I_d$ is less than $I_2$ are categorized as having an intensity score of "2," which is the low rank.

Furthermore, as for the mass-to-charge ratio (m/z) of known compounds, the mass-to-charge ratio (m/z) of each peak in the $MS^n$ mass spectra is found by the position score calculation unit 31c.

As a result, an intensity score and a mass-to-charge ratio (m/z) are assigned, respectively, to all of the peaks in such a manner that the intensity score "4" and the mass-to-charge ratio $(m_{(i+1)}/z_{(i+1)})$ are assigned to the $i^{th}$ peak and the intensity score "2" and the mass-to-charge ratio $(m_i/z_i)$ are assigned to the $(i+1)^{th}$ peak, for example. Thus, an intensity score and a mass-to-charge ratio (m/z) are assigned, respectively, to all of the peaks of the $MS^n$ mass spectra of all of the known compounds.

Figure 2:
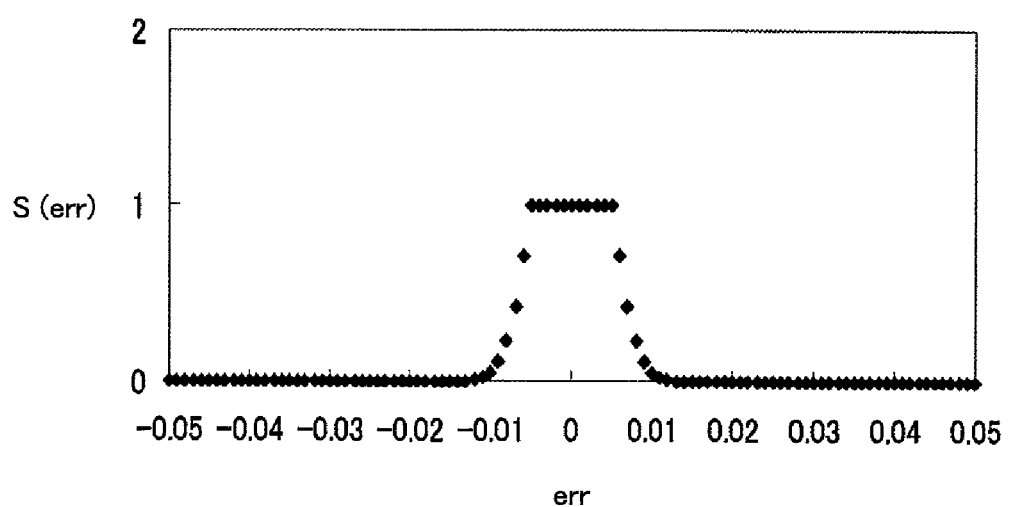
FIG. 2 is a graph showing an example of a distribution function stored in the distribution function storage region.

FIG. 2 is a graph showing an example of the distribution function stored in the distribution function storage region 32d. The lateral axis is the difference err in the mass-to-charge ratio m/z, and the longitudinal axis is the position score S (err). The distribution function makes the difference err "0" correspond to the position score "1" and the greater the difference err is, the lower the position score is, in such a manner as to approach the position score of "0."

The acquisition unit 31a carries out $MS^n$ analysis on an unknown compound (n=2, 3, 4, . . . ) and, thus, carries out such control that the ion intensity $I_q$ acquired by the detector 23 is stored in the memory 32 and, after that, an $MS^n$ mass spectrum wherein the ion intensity $I_q$ is along the longitudinal axis and m/z is along the lateral axis is prepared and stored in the unknown compound data storage region 32b.

The intensity score calculation unit 31b carries out such control that each peak in the $MS^n$ mass spectrum of the unknown compound is categorized into one of the intensity scores of three ranks depending on the degree of the ion intensity $I_q$ (n=2, 3, 4, Concretely, peaks of which the ion intensity $I_q$ is $I_1$ or greater are categorized as having an intensity score of "4," which is the high rank, peaks of which the ion intensity $I_q$ is $I_2$ or greater and less than $I_1$ are categorized as having an intensity score of "3," which is the middle rank, and peaks of which the ion intensity $I_q$ is less than $I_2$ are categorized as having an intensity score of "2," which is the low rank.

The neutral loss calculation unit 31e carries out such control as to find a peak of neutral loss in the MS" mass spectrum of the unknown compound. For example, an ion having an appropriate mass-to-charge ratio (m/z) is automatically selected as a precursor ion from among ions originating from each sample component, or an ion having a peak of the mass-to-charge ratio (m/z) that has been designated in advance is selected as a precursor ion, and neutral loss is found from the mass-to-charge ratio (m/z) of the peak and the mass of the precursor ion for the gained MS" mass spectrum of the unknown compound. As a result, an MS" mass spectrum of the unknown compound that includes the peak of neutral loss is prepared (n=2, 3, 4, . . . ). Here, the ion intensity I of the peak of neutral loss to be added to the MS" mass spectrum is the same ion intensity I as that of the original peak, for example.

The position score calculation unit 31c caries out such control that a position score S (err) indicating an error of the mass-to-charge ratio (m/z) is found for each peak on the basis of the difference err between the mass-to-charge ratio (m/z) of the peak in the MS" mass spectrum of a known compound and the mass-to-charge ratio (m/z) of the corresponding peak in the MS" mass spectrum of the unknown compound (including the peak of neutral loss).

First, the mass-to-charge ratio (m/z) is found for each peak (including the peak of neutral loss) for the MS" mass spectrum of the unknown compound stored in the unknown compound data storage region 32b.

Next, the MS" mass spectrum of the unknown compound is sequentially compared to the MS" mass spectrum of each of various known compounds. When the MS" mass spectrum of the $X^{th}$ known compound is compared to the MS" mass spectrum of the unknown compound, the peak (including the peak of neutral loss) of the mass-to-charge ratio (m/z) that is the closest to the mass-to-charge ratio (m/z) of $i^{th}$ peak in the MS" mass spectrum of the $X^{th}$ known compound is found. For example, the $j^{th}$ peak in the MS" mass spectrum of the unknown compound is found as the peak of the mass-to-charge ratio (m/z) that is closest to the mass-to-charge ratio (m/z) of the $i^{th}$ peak in the MS" mass spectrum of the $X^{th}$ known compound. Thus, the position score $S_{ij}$ (err) is found by calculating the difference err between the mass-to-charge ratio (m/z) of the $i^{th}$ peak in the MS" mass spectrum of the $X^{th}$ known compound and the mass-to-charge ratio (m/z) of the $j^{th}$ peak in the MS" mass spectrum of the unknown compound, and by substituting the difference err into the distribution function in FIG. 2.

Furthermore, the peak of the mass-to-charge ratio (m/z) that is the closest the mass-to-charge ratio (m/z) of the $(i+1)^{th}$ peak in the MS" mass spectrum of the $X^{th}$ known compound (including the peak of neutral loss) is found. For example, the $(j+n)^{th}$ peak in the MS" mass spectrum of the unknown compound is found as the peak of the mass-to-charge ratio (m/z) that is the closest to the mass-to-charge ratio (m/z) of the $(i+1)^{th}$ peak in the MS" mass spectrum of the $X^{th}$ known compound. Thus, the position score $S_{(i+1)(j+n)}$(err) is found by calculating the difference err between the mass-to-charge ratio (m/z) of the $(i+1)^{th}$ peak in the MS" mass spectrum of the $X^{th}$ known compound and the mass-to-charge ratio (m/z) of the $(j+n)^{th}$ peak in the MS" mass spectrum of the unknown compound, and by substituting the difference err into the distribution function in FIG. 2.

In this manner the corresponding peak in the MS" mass spectrum of the unknown compound (including the peak of neutral loss) is found for all of the peaks in the MS" mass spectrum of the $X^{th}$ known compound so as to find the position score S(err).

The peak score calculation unit 31f carries out such control as to find the peak score S(N) according to the following formula (1).

$$S(N) = (\text{number of matched peaks/number of peaks in MS}^n \text{ mass spectra of known compounds}) \times 100 \quad (1)$$

As a result, the peak score S(N) indicating the degree of matching is found from the number of matched pairs between the mass-to-charge ratio (m/z) of a peak in the MS" mass spectra of known compounds and a peak in the MS" mass spectrum of the unknown compound (including the peak of neutral loss). For example, when the number of peaks in the MS" mass spectrum of the $X^{th}$ known compound is 5 and the number of matched peaks is 3, the peak score indicating the degree of matching is 60. When the number of peaks in the MS" mass spectrum of the $(X+1)^{th}$ known compound is 10 and the number of matched peaks is 1, the peak score indicating the degree of matching is 10.

Here, "matched" means that a peak of which the position score S(err) is not 0 or a peak of neutral loss exists in the MS" mass spectrum of the unknown compound for a certain peak in the MS" mass spectra of known compounds.

The score calculation unit 31d carries out such control as to calculate the score Scr according to the following formula (2)f $$\text{Scr} = S_{ij}(\text{err}) \times I_{dj} \times I_{qi} + S_{(i+1)(j+n)}(\text{err}) \times I_{d(i+1)} \times I_{q(j+n)} + \ldots + S(N) \quad (2)$$

Here, "$I_{di}$" is the intensity score of the $i^{th}$ peak in the MS" mass spectrum of a known compound, "$I_{d(i+1)}$" is the intensity score of the $(i+1)^{th}$ peak in the MS" mass spectrum of the known compound, "$I_{qi}$" is the intensity score of the $j^{th}$ peak in the MS" mass spectrum of the unknown compound and "$I_{q(j+n)}$" is the intensity score of the $(j+n)^{th}$ peak in the MS" mass spectrum of the unknown compound.

As a result, the intensity score $I_d$ of each peak in the MS" mass spectrum of a known compound, the intensity score $I_q$ of the peak in the MS" mass spectrum of the unknown compound and the position score S(err) are added up, and the total sum of the values that have been added up is calculated for all of the peaks and, then, the peak score S(N) is added to the thus calculated value so that the score Scr indicating the similarity between the unknown compound and the $X^{th}$ known compound is calculated. Thus, scores Scr indicating the similarity between the MS" mass spectrum of the unknown compound the MS" mass spectra of the various known compounds are calculated.

Figure 3A:
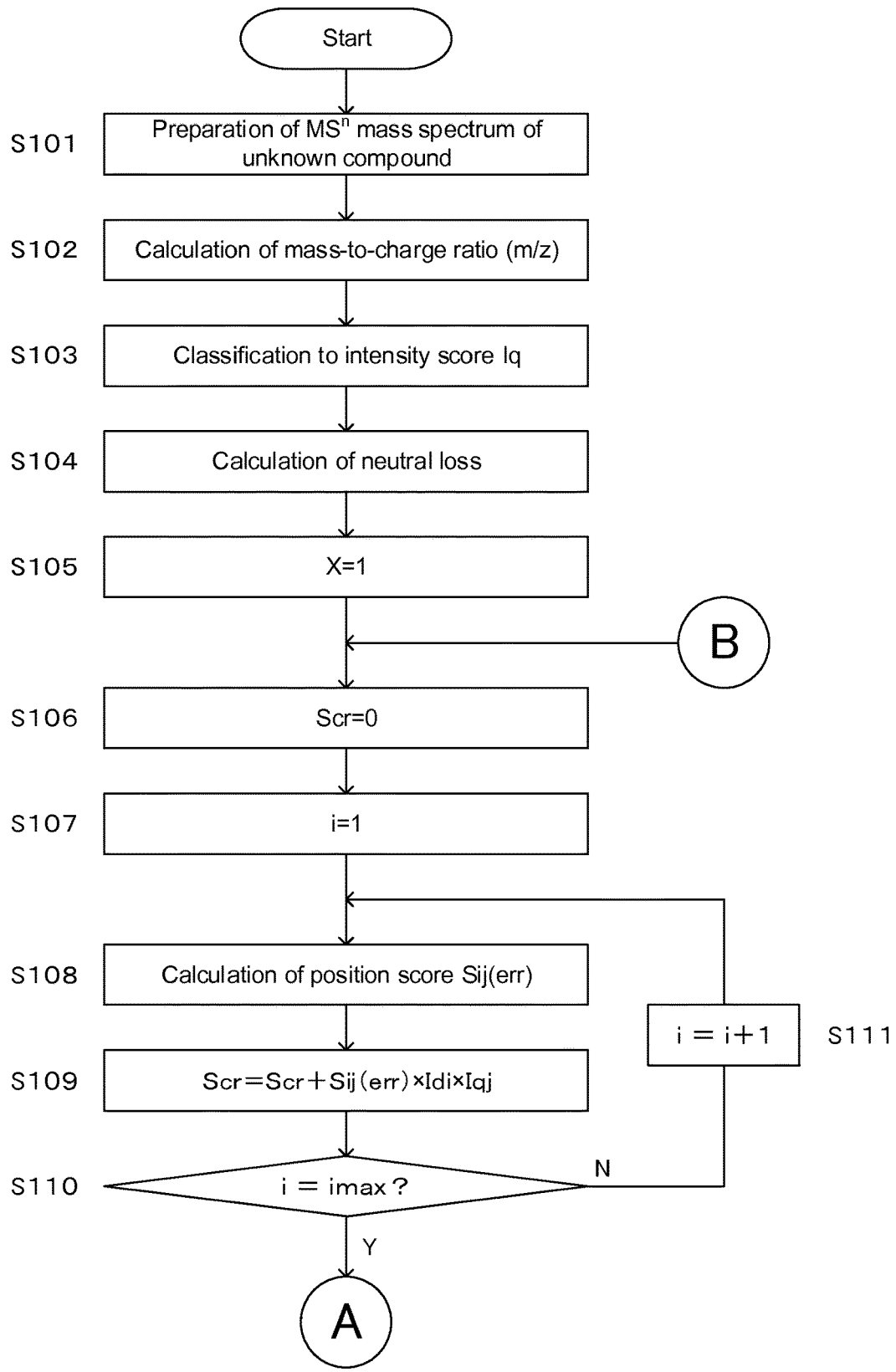
FIG. 3A is a flowchart for describing an example of the data processing method.
Figure 3B:
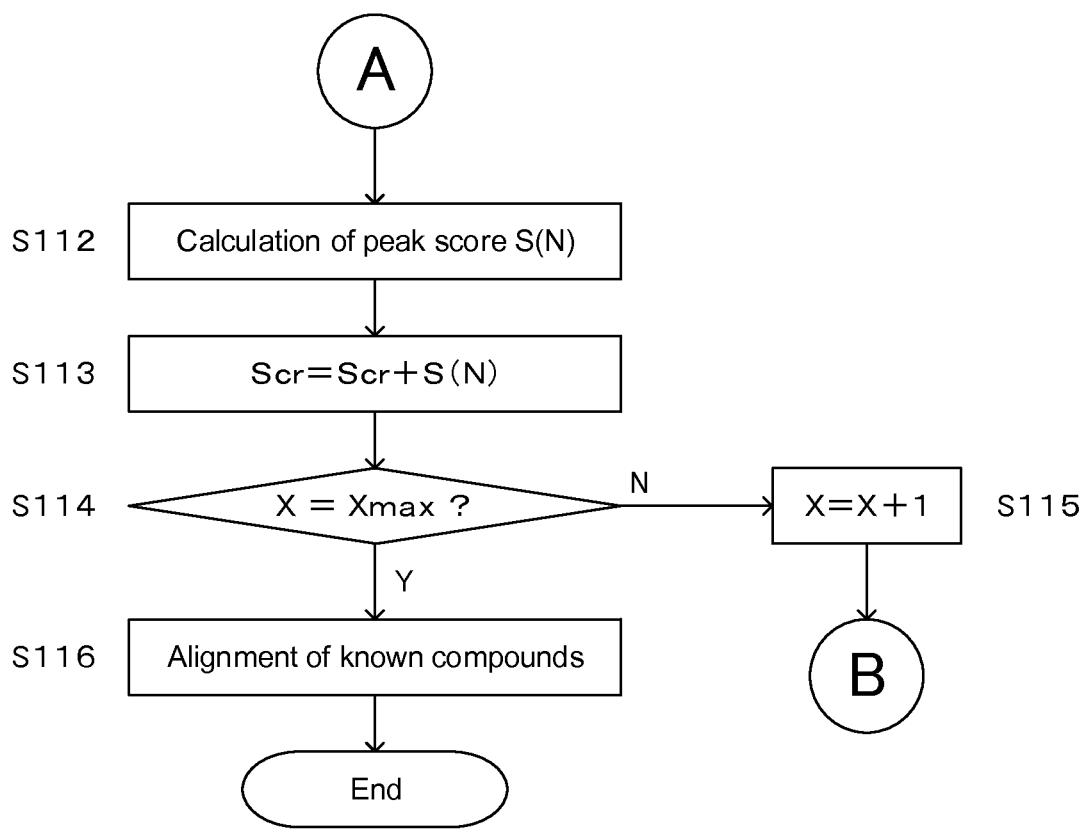
FIG. 3B is a flowchart for describing another example of the data processing method.

Here, the data processing method for identifying the unknown compound using the liquid chromatography-mass spectrometer (LC/MS) 1 is described. FIG. 3 is a flowchart for illustrating an example of the data processing method.

First, in the process of Step S101, the MS" mass spectrum of the unknown compound is prepared (n=2, 3, 4, . . . ).

Next, in the process of Step S102, the mass-to-charge ratio (m/z) is found for each peak in the MS" mass spectrum of the unknown compound.

Next, in the process of Step S103, each peak in the MS" mass spectrum of the unknown compound is categorized into one of the three ranks of the intensity score depending on the degree of the ion intensity $I_q$ (intensity score calculation step).

Next, in the process of Step S104, the peak of neutral loss in the MS" mass spectrum of the unknown compound is found (neutral loss calculation step).

Next, in the process of Step S105, the known compound order parameter X indicating the order known compounds is set to 1, wherein X=1.

Next, in the process of Step S106, the score Scr is set to 0, wherein Scr=0.

Next, in the process of Step S107, the peak order parameter i indicating the order of peaks in the MS$^n$ mass spectrum of a known compound is set to 1, wherein i=1.

Next, in the process of Step S108, the peak of the mass-to-charge ratio (m/z) that is the closest to the mass-to-charge ratio (m/z) of the i$^{th}$ peak in the MS$^n$ mass spectrum of a known compound is found. Then, the position score $S_{ij}$(err) is found by calculating the difference err between the mass-to-charge ratio (m/z) of the i$^{th}$ peak in the MS$^n$ mass spectrum of a known compound and the mass-to-charge ratio (m/z) of the j$^{th}$ peak in the MS$^n$ mass spectrum of the unknown compound and by substituting the difference err into the distribution function in FIG. 2 (position score calculation step).

Next, in the process of Step S109, Scr is found wherein Scr=Scr+$S_{ij}$(err)×$I_{di}$×$I_{qj}$.

Next, in the process of Step S110, whether or not i=$i_{max}$ (peak coming last in the order in the MS$^n$ mass spectrum of a known compound) is determined. When it is determined that i=$i_{max}$ does not hold true, i is increased by 1 wherein i=i+1 in the process of Step S111 and the process returns to Step S108.

Meanwhile, when it is determined that i=$i_{max}$ holds true, the peak score S(N) is found according to the formula (1) in the process of Step S112 (peak score calculation step).

Next, in the process of Step S113, Scr is substituted with Scr+S(N) wherein Scr=Scr+S(N) (score calculation step).

Next, in the process of Step S114, it is determined whether or not X=$X_{max}$ holds true (known compound coming last in the order). When it is determined that X=$X_{max}$ does not hold true, X is substituted with X+1 wherein X=X+1 in the process of Step S115 and the process returns to Step S106.

Meanwhile, when it is determined that X=$X_{max}$ holds true, the known compounds are aligned in descending order starting from the highest score Scr.

When the process in Step S116 has been completed, the present flowchart is complete.

As described above, the liquid chromatography-mass spectrometer (LC/MS) 1 can allow the similarity between the MS$^n$ mass spectrum of the unknown compound and the MS$^n$ mass spectra of a great number of known compounds to be correctly evaluated even when the ion intensity $I_q$ of a peak in the MS$^n$ mass spectrum of the unknown compound, the peak position (m/z) and the existence of a peak have changed.

Other Embodiments (1) Though the above described liquid chromatography-mass spectrometer (LC/MS) 1 has such a configuration that the intensity score calculation unit 31$b$ classifies, respectively, each peak in the MS$^n$ mass spectrum of the unknown compound and each peak in the MS$^n$ mass spectra of known compounds into one of the three ranks of the intensity score depending on the degree of the ion intensity $I_q$ or $I_d$ (n=2, 3, 4, . . . ), the configuration may allow each peak to be categorized into one of two ranks or into one of four ranks of the intensity score depending on the log value transformed from the ion intensity $I_q$ or $I_d$. Furthermore, the intensity score calculation unit may have such a configuration that peaks of which the degree of ion intensity $I_q$ is no greater than the threshold value are removed from the MS$^n$ mass spectrum of the unknown compound.

(2) Though the above described liquid chromatography-mass spectrometer (LC/MS) 1 has such a configuration that the intensity score calculation unit 31$b$ classifies, respectively, each peak in the MS$^n$ mass spectrum of the unknown compound and each peak in the MS$^n$ mass spectra of known compounds into one of the three ranks of the intensity score depending on the degree of the ion intensity $I_q$ or $I_d$ (n=2, 3, 4, . . . ), the configuration may allow each peak to be categorized into one of several ranks of the intensity score depending on the degree of the ion intensity $I_q$ or $I_d$ and the value of the mass-to-charge ratio of the peak. For example, peaks of which the ion intensity $I_q$ or $I_d$ is $I_1$ or greater are categorized as having an intensity score of "4," which is the high rank, peaks of which the ion intensity $I_q$ or $I_d$ is $I_2$ or greater and less than $I_1$ are categorized as having an intensity score of "3," which is the middle rank, and peaks of which the ion intensity $I_q$ or $I_d$ is less than $I_2$ are categorized as having an intensity score of "2," which is the low rank and, at the same time, the intensity score "2" is added to the peaks of which the mass-to-charge ratio is no less than $m_1/z_1$ and the intensity score "1" is added to the peaks of which the mass-to-charge ratio is less than $m_1/z_1$.

(3) The above described liquid chromatography-mass spectrometer (LC/MS) 1 may have such a configuration wherein the intensity score calculation unit corrects the mass-to-charge ratio of a peak in the MS$^n$ mass spectrum of the unknown compound using the mass of an adduct ion.

(4) Though the above described liquid chromatography-mass spectrometer (LC/MS) 1 has such a configuration wherein the peak score S(N) is found according to the formula (1), the configuration may allow the peak score S(N), which increases as the number of matched pairs increases, to be found. In the case wherein 80% or more of the peaks in the MS$^n$ mass spectrum of a known compound match, for example, the peak score is set to "100," in the case wherein 50% or more and less than 80% of the peaks in the MS$^n$ mass spectrum of a known compound match, the peak score is set to "50," and in the case wherein 20% of the peaks in the MS$^n$ mass spectrum of a known compound match, the peak score is set to "20."

(5) The above described liquid chromatography-mass spectrometer (LC/MS) 1 may have such a configuration wherein the score calculation unit finds, respectively, the scores of the MS$^{n+m}$ mass spectrum indicating similarities between the MS$^{n+m}$ mass spectrum of the unknown compound and the MS$^{n+m}$ mass spectra of a great number of known compounds, and adds the score of the MS$^{n+m}$ mass spectrum to the score of the MS$^n$ mass spectrum.

INDUSTRIAL APPLICABILITY

The present invention can be applied to a data processing method for finding, respectively, scores indicating similarities between the MS$^n$ mass spectrum of an unknown compound and the MS$^n$ mass spectra of a great number of known compounds that have been gained by a mass spectrometer and for identifying the unknown compound on the basis of the scores.

EXPLANATION OF SYMBOLS

1: liquid chromatography-mass spectrometer (data processing device)
31$a$: acquisition unit
31$b$: intensity score calculation unit 31c: position score calculation unit
31d: score calculation unit
32c: data base storage region

The invention claimed is:

1. A chromatograph spectrometer comprising:
a chromatograph comprising a column configured to separate an unknown compound;
a mass spectrometer configured to mass separate the unknown compound and perform $MS^n$ analysis to generate a $MS^n$ mass spectrum of the unknown compound;
a data processing device, comprising:
a data base storage region for storing $MS^n$ mass spectra of a great number of known compounds in advance; and
a central processing unit (CPU) configured to execute instructions to:
acquire the $MS^n$ mass spectrum of the unknown compound; and
find respective scores indicating similarities between the $MS^n$ mass spectrum of the unknown compound and $MS^n$ mass spectra of the great number of known compounds, characterized by further comprising:
classify the peaks in the $MS^n$ mass spectrum of the unknown compound and the peaks in the $MS^n$ mass spectra of the known compounds into intensity scores of several ranks depending on the dimensions of the ion intensities, respectively;
find a peak of a neutral loss in the $MS^n$ mass spectrum of the unknown compound; and
find the respective position scores indicating error in the mass-to-charge ratio for each peak on the basis of the difference between the mass-to-charge ratio of each peak that includes the peak of said neutral loss in the $MS^n$ mass spectra of the known compounds and the mass-to-charge ratio of the corresponding peak in the $MS^n$ mass spectrum of the unknown compound, wherein
the CPU adds up the intensity score of each peak in the $MS^n$ mass spectrum of a known compound, the intensity score of the corresponding peak in the $MS^n$ mass spectrum of the unknown compound and the position score, and calculates as a score the sum total of the values that have been added up for all peaks, and
wherein the CPU identifies the unknown compound based on said score.

2. The chromatograph spectrometer according to claim 1, characterized by the CPU further being configured to calculate a peak score indicating the degree of matching on the basis of the degree of matching found from the number of matching pairs regarding the mass-to-charge ratio of each peak in the $MS^n$ mass spectrum of a known compound and the mass-to-charge ratio of the corresponding peak in the $MS^n$ mass spectrum of the unknown compound, wherein
said CPU adds said peak score to said score.

3. The chromatograph spectrometer according to claim 1, characterized in that said CPU classifies each peak in the $MS^n$ mass spectrum of the unknown compound and each peak in the $MS^n$ mass spectra of the known compounds into intensity scores of three or several ranks, respectively, depending on the ion intensity or the log value transformed from the ion intensity.

4. The chromatograph spectrometer according to claim 1, characterized in that said CPU classifies each peak in the $MS^n$ mass spectrum of the unknown compound and each peak in the $MS^n$ mass spectra of the known compounds into intensity scores of several ranks, respectively, depending on the degree of the ion intensity and the value of the mass-to-charge ratio of the peak.

5. The chromatograph spectrometer according to claim 1, characterized in that said CPU removes a peak of which the degree of ion intensity is of a threshold value or less from the $MS^n$ mass spectrum of the unknown compound.

6. The chromatograph spectrometer according to claim 1, characterized in that said CPU sets the mass-to-charge ratio of a peak in the $MS^n$ mass spectra of the known compounds as a reference value and, respectively, finds a position score of which the value is lower as the position is further away from the reference value for each peak in the $MS^n$ mass spectrum of the unknown compound.

7. The chromatograph spectrometer according to claim 1, characterized in that said CPU corrects the mass-to-charge ratio of a peak in the $MS^n$ mass spectrum of the unknown compound using the mass of an adduct ion.

8. The chromatograph spectrometer according to claim 2, characterized in that said CPU finds a peak score that increases as the number of matching pairs increases.

9. The chromatograph spectrometer according to claim 1, characterized in that said CPU, respectively, finds a score of the $MS^{n+m}$ mass spectrum indicating similarity between the $MS^{n+m}$ mass spectrum of the unknown compound and the $MS^{n+m}$ mass spectra of the great number of known compounds, and adds the score of the $MS^{n+m}$ mass spectra to the $MS^n$ mass spectra.

10. A chromatograph spectrometer data processing method, using a data processing device, that comprises:
separating an unknown compound by a chromatograph;
mass separating the unknown compound and performing $MS^n$ analysis to generate a $MS^n$ mass spectrum of the unknown compound by a mass spectrometer;
storing $MS^n$ mass spectra of a great number of known compounds in advance in a data base storage;
acquiring the $MS^n$ mass spectrum of the unknown compound; and
finding respective scores indicating similarities between the $MS^n$ mass spectrum of the unknown compound and $MS^n$ mass spectra of the great number of known compounds, comprising:
classifying the peaks in the $MS^n$ mass spectrum of the unknown compound and the peaks in the $MS^n$ mass spectra of the known compounds into intensity scores of several ranks depending on the dimensions of the ion intensities, respectively;
finding a peak of a neutral loss in the $MS^n$ mass spectrum of the unknown compound;
finding the respective position scores indicating error in the mass-to-charge ratio for each peak on the basis of the difference between the mass-to-charge ratio of each peak that includes the peak of said neutral loss in the $MS^n$ mass spectra of the known compounds and the mass-to-charge ratio of the corresponding peak in the $MS^n$ mass spectrum of the unknown compound; and
adding up the intensity score of each peak in the $MS^n$ mass spectrum of a known compound, the intensity score of the corresponding peak in the $MS^n$ mass spectrum of the unknown compound and the position score, and of calculating as a score the sum total of the values that have been added up for all peaks; and
identifying the unknown compound based on said score.

11. The chromatograph mass spectrometer data processing method according to claim 10, characterized by further comprising:

finding a peak score indicating the degree of matching on the basis of the degree of matching found from the number of matching pairs regarding the mass-to-charge ratio of each peak in the MS$^n$ mass spectrum of a known compound and the mass-to-charge ratio of the corresponding peak in the MS$^n$ mass spectrum of the unknown compound; and adding said peak score to said score.

\* \* \* \* \*